United States Patent
Lee et al.

(10) Patent No.: US 8,890,089 B2
(45) Date of Patent: Nov. 18, 2014

(54) FAECAL MARKERS

(75) Inventors: Michael Lee, Lampeter (GB); Michael Theodorou, Tregaron (GB); Helen Ougham, Aberystwyth (GB); Howard Thomas, Aberystwyth (GB)

(73) Assignee: Aberystwyth University, Aberystwyth (GB)

( * ) Notice: Subject to any disclaimer, the term of this patent is extended or adjusted under 35 U.S.C. 154(b) by 57 days.

(21) Appl. No.: 13/255,288

(22) PCT Filed: Mar. 9, 2010

(86) PCT No.: PCT/GB2010/000412
§ 371 (c)(1),
(2), (4) Date: Nov. 12, 2011

(87) PCT Pub. No.: WO2010/103261
PCT Pub. Date: Sep. 16, 2010

(65) Prior Publication Data
US 2012/0061588 A1 Mar. 15, 2012

(30) Foreign Application Priority Data
Mar. 9, 2009 (GB) .................................. 0904024.7

(51) Int. Cl.
G01N 21/64 (2006.01)
G01N 33/12 (2006.01)
C09B 61/00 (2006.01)

(52) U.S. Cl.
CPC ............... *C09B 61/00* (2013.01); *G01N 33/12* (2013.01)
USPC .................................................... 250/459.1

(58) Field of Classification Search
CPC ...... G01N 21/6486; G01N 21/64; A23K 1/00
USPC ........................................................ 250/459.1
See application file for complete search history.

(56) References Cited

U.S. PATENT DOCUMENTS 5,621,215 A * 4/1997 Waldroup et al. .......... 250/461.2
5,658,798 A 8/1997 Bertin et al.
(Continued)

FOREIGN PATENT DOCUMENTS

JP 2002 047197 2/2002
WO 2007/033227 3/2007

OTHER PUBLICATIONS

Kim et al., Journal of Food Protection, 66(7):1198-1207 (2003). "Optimal Fluorescence Excitation and Emission Bands for Detection of Fecal Contamination."

*Primary Examiner* — Marcus Taningco
(74) *Attorney, Agent, or Firm* — Nixon Peabody LLP.

(57) ABSTRACT

Described are methods for analyzing an animal carcass, meat obtained therefrom, or product produced by or obtained from an animal for the presence or absence of faecal matter. The methods comprise analyzing an animal carcass, meat obtained therefrom, or product produced by or obtained from the animal for the presence or absence of a detectable marker, the presence of the detectable marker being indicative of the presence of faecal matter and the absence of the detectable marker being indicative of the absence of faecal matter, wherein the animal carcass, meat obtained therefrom, or product produced by or obtained from the animal has been obtained from an animal fed a composition comprising a supplement of the detectable marker and/or a precursor thereof. Also described are compositions for feeding to an animal and for use in the methods.

13 Claims, 6 Drawing Sheets

(56) References Cited

U.S. PATENT DOCUMENTS

| | | |
|---|---|---|
| 5,821,546 A | 10/1998 | Xiao et al. |
| 5,846,830 A | 12/1998 | Demello et al. |
| 5,895,921 A * | 4/1999 | Waldroup et al. .......... 250/461.2 |
| 5,914,247 A * | 6/1999 | Casey et al. ..................... 435/34 |
| 2003/0160182 A1* | 8/2003 | Petrich et al. .............. 250/458.1 |
| 2003/0164456 A1* | 9/2003 | Petrich et al. .............. 250/458.1 |
| 2004/0248285 A1* | 12/2004 | Casey et al. ................ 435/287.2 |

\* cited by examiner

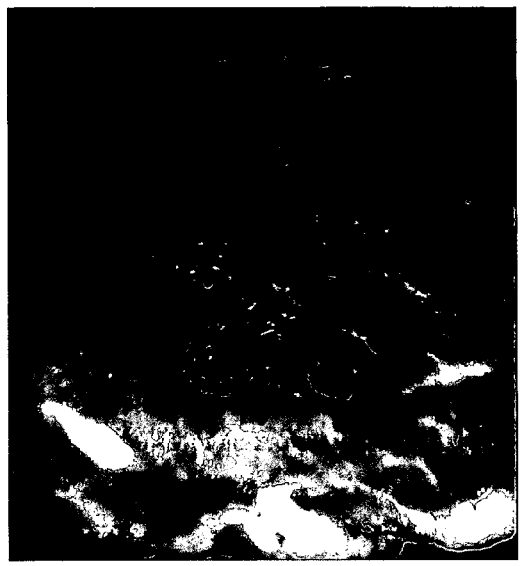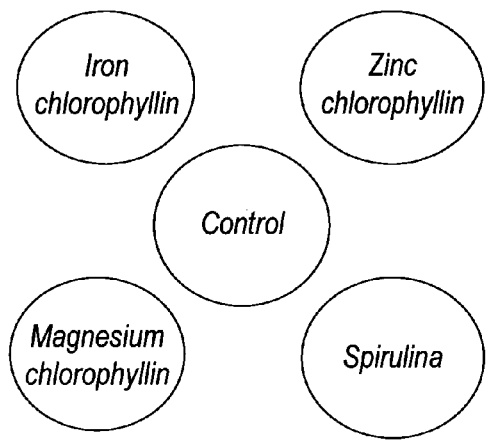
*Fig.3*
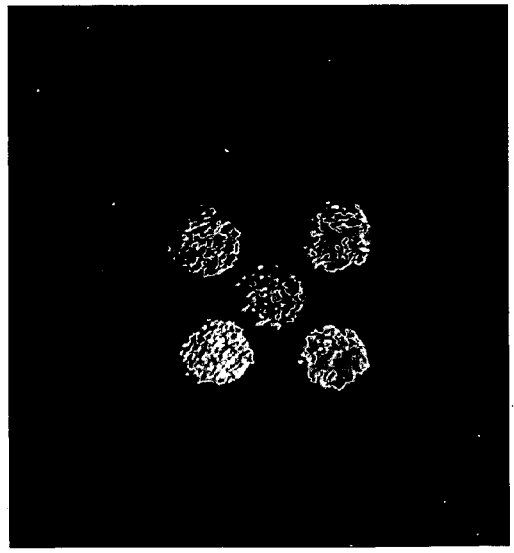
*Fig.4A*  *Fig.4B*

FAECAL MARKERS

CROSS REFERENCE TO RELATED APPLICATIONS

This application is a 35 U.S.C. §371 National Phase Entry Application of International Application No. PCT/GB2010/000412 filed Mar. 9, 2010, which designates the U.S., and which claims the benefit of Great Britain Application No. 0904024.7 filed Mar. 9, 2009, the contents of which are incorporated herein by reference in its entirety.

BACKGROUND OF THE INVENTION

The present application relates to compositions and methods for detecting faecal contamination in animal carcasses, meat obtained therefrom and products produced by or obtained from animals in particular to faecal markers for use in such methods and compositions.

Cleanliness in the abattoir is of the utmost importance and numerous practices are carried out on farms to ensure that the animals arrive at the abattoir with limited faecal matter clinging to the hide. Such strategies include: change to hay and cereal based diets before slaughter to encourage 'dry' faeces; cleaning the animals before they travel; reducing stress on the animals during transport and at the abattoir to limit pathogen shedding. However, even with these strategies in place, a major source of contamination in the abattoir is from small traces of faeces still associated with the hide coming into contact with the dressed carcass. Currently carcasses are checked by 'eye' and washed with chemical sprays or dissected to remove contaminated areas. This runs the risk of missing small areas of faecal contamination which could harbour lethal pathogens such as *E. coli, Listeria monocytogenes* and *Campylobacter*. The problems are prevalent in the processing of various animals, including, for example, cattle and poultry. In the case of poultry, and in particular chickens, the presence of faecal contamination on eggs is also of concern.

A known method, called Verifeye®, uses natural levels of chlorophyll to visualise faecal contaminants. However this technology has not been universally accepted due to the variation of chlorophyll in different diets. For example the difference in the amount of fluorescence between animals grazing fresh pasture and animals on a barley beef system would be huge meaning that it is not possible to accurately attribute actual fluorescence to faecal spoilage. One such method is described in International patent application number PCT/US99/03961, published under the number WO99/45138.

Thus, a need exists for improved methods of detecting faecal contaminants in meat. In particular methods are needed which can be used in detecting faecal contaminants during the processing of animal carcasses from a variety of animals and production systems.

SUMMARY OF THE INVENTION

According to one aspect of the present invention, there is provided a method for analysing an animal carcass, meat obtained therefrom, or a product produced by or obtained from an animal for the presence or absence of faecal matter, the method comprising:

analysing the animal carcass, meat obtained therefrom, or product produced by or obtained from the animal for the presence or absence of a detectable marker, the presence of the detectable marker being indicative of the presence of faecal matter and the absence of the detectable marker being indicative of the absence of faecal matter;

wherein the animal carcass, meat obtained therefrom, or product produced by or obtained from the animal has been obtained from an animal fed a composition comprising a supplement of the detectable marker and/or a precursor thereof.

The present invention provides a reliable and reproducible method for detecting the presence or absence of faecal matter on an animal carcass, meat obtained therefrom, or product produced by or obtained from the animal. Unlike known methods, the present invention is unlikely to produce false negatives which may have occurred in known methods due to the variation of detectable markers, e.g. chlorophyll, in different diets, or indeed false positives which may have occurred due to the presence of low levels of haemoglobin metabolism degradation products which were unrelated to faecal contamination. In the embodiments of the present invention, a single compound, or group of compounds, can be pin pointed as a specific marker of faecal contamination.

Preferably, the product is selected from meat, eggs or milk produced by or obtained from the animal.

As a result of the improved cleanliness of produce obtained using the methods of the present invention, the level of spoilage organisms is greatly reduced and thus the shelf life of said produce can be increased.

According to another aspect of the present invention, there is provided a composition for feeding to an animal and for use in a method of the present invention, the composition comprising a supplement of a detectable marker and/or a precursor thereof.

Preferably, the detectable marker comprises a fluorescent marker.

Preferably, the detectable marker comprises a porphyrin ring or a derivative, analogue or homologue thereof, or salt thereof. As such, it is preferred that the fluorescent marker comprises the structure shown in Formula I or a derivative, analogue or homologue thereof, or salt thereof, wherein R is absent or is a metal ion. Preferably R is a divalent metal ion, for example an alkaline earth metal, such as Mg, or a transition metal, such as Fe, Cu, Zn, Pd, Co, Ni and Mn. Preferably R is selected from magnesium, iron, zinc or copper, for example $Mg^{2+}$, $Fe^{2+}$, $Zn^{2+}$ or $Cu^{2+}$. Further preferably, R is selected from magnesium, iron or zinc, more preferably magnesium or zinc, most preferably magnesium.

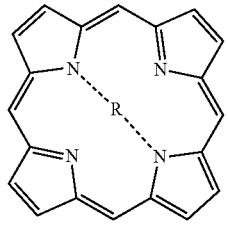

Formula I

It will be appreciated that throughout this specification, the use of a dotted line represents an optional bond. As such, in relation to Formula I, the structure may be provided with or without R. Put another way, the structure of Formula I could be either of the structures set out below and designated as Formula IA and IB.

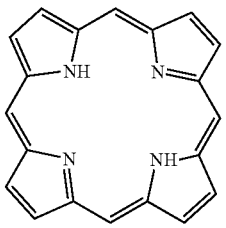

Formula IA

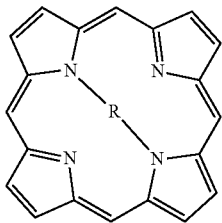

Formula IB

Preferably, the detectable marker comprises the structure shown in Formula IIA or IIB or a derivative, analogue or homologue thereof, or a salt thereof.

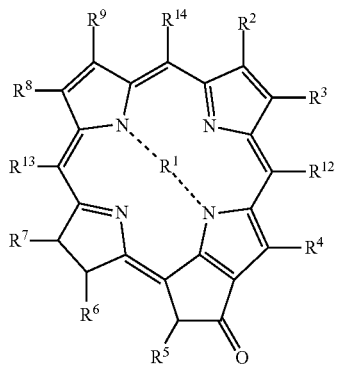

Formula IIA

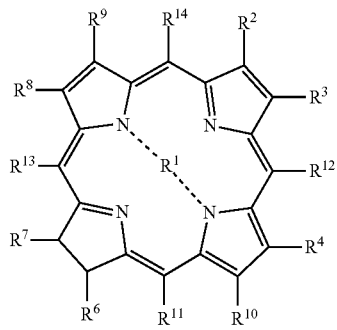

Formula IIB

Preferably, $R^1$ is absent or is a metal ion, preferably a divalent metal ion, for example an alkaline earth metal, such as Mg, or a transition metal, such as Fe, Cu, Zn, Pd, Co, Ni and Mn. Preferably R is selected from magnesium, iron, zinc or copper, for example $Mg^{2+}$, $Fe^{2+}$, $Zn^{2+}$ or $Cu^{2+}$. Further preferably, R is selected from magnesium, iron or zinc, more preferably magnesium or zinc, most preferably magnesium;

$R^2$ is selected from (i) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, (ii) an aldehyde, preferably containing from 1 to about 20 carbon atoms, more preferably from 1 to about 10 carbon atoms, further preferably from 1 to about 6 carbon atoms, further preferably from 1 to about 3 carbon atoms, for example —CHO or —$R^{17}$CHO, where $R^{17}$ is preferably an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, (iii) a hydrogen, and (iv) an ester, for example —C(O)$OR^{15}$ or —$R^{16}$C(O)$OR^{15}$, where $R^{15}$ is selected from (a) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, and (b) hydrogen, and where $R^{16}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S;

$R^3$ is selected from (i) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, (ii) an alkenyl, preferably containing from 2 to about 20 carbon atoms, more preferably from 2 to about 10 carbon atoms, further preferably from 2 to about 6 carbon atoms, further preferably from 2 to about 4 carbon atoms, for example ethenyl or propenyl, which may be linear or branched and may contain one or more heteroatoms, for example O, NH or S, (iii) a hydrogen, and (iv) an ester, for example —C(O)$OR^{15}$ or —$R^{16}$C(O)$OR^{15}$, where $R^{15}$ is selected from (a) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, and (b) hydrogen, and where $R^{16}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S;

$R^4$, $R^7$, $R^8$, $R^{10}$, $R^{11}$, $R^{12}$, $R^{13}$ and $R^{14}$ are the same or different and selected from (i) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, (ii) a hydrogen, and (iii) an ester, for example —C(O)$OR^{15}$ or —$R^{16}$C(O)$OR^{15}$, where $R^{15}$ is selected from (a) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, and (b) hydrogen, and where $R^{16}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S;

$R^5$ is selected from (i) an ester, for example —C(O)OR$^{15}$ or —R$^{16}$C(O)OR$^{15}$ and (ii) a hydrogen, where $R^{15}$ is selected from (a) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, and (b) hydrogen, and where $R^{16}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S;

$R^6$ is selected from (i) hydrogen and (ii) an ester, for example —C(O)OR$^{15}$ or —R$^{16}$C(O)OR$^{15}$, where $R^{15}$ is selected from (a) an alkyl, preferably containing from 1 to about 50 carbon atoms, more preferably from about 10 to about 40 carbon atoms, further preferably from about 20 to about 30 carbon atoms, further preferably from about 20 to about 25 carbon atoms, most preferably about 20 carbon atoms, which may be linear or branched and may contain one or more heteroatoms, for example O, NH or S, (b) an alkenyl, preferably containing from 2 to about 50 carbon atoms, more preferably from about 10 to about 40 carbon atoms, further preferably from about 20 to about 30 carbon atoms, further preferably from about 20 to about 25 carbon atoms, most preferably about 20 carbon atoms, which may be linear or branched and may contain one or more heteroatoms, for example O, NH or S, and (c) hydrogen, and where $R^{16}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S or an alkenyl, preferably containing from 2 to about 20 carbon atoms, more preferably from 2 to about 10 carbon atoms, further preferably from 2 to about 6 carbon atoms, further preferably from 2 to about 4 carbon atoms, for example ethenyl, propenyl, which may be linear or branched and may contain one or more heteroatoms, for example O, NH or S. In particular embodiments, $R^{15}$ is —CH$_2$CH═C(CH$_3$)—[CH$_2$CH$_2$CH$_2$C(CH$_3$)]$_n$—CH$_3$, wherein n is an integer from 1 to about 10, preferably, from 1 to about 6, preferably from 1 to about 4, preferably 3. In particular embodiments, $R^6$ is selected from hydrogen and CH$_2$CH$_2$C(O)OCH$_2$CH$^2$CH═C(CH$_3$)—[CH$_2$CH$_2$CH$_2$C(CH$_3$)]$_n$—CH$_3$ wherein n is an integer from 1 to about 10, preferably, from 1 to about 6, preferably from 1 to about 4, preferably 3; and $R^9$ is selected from (i) an alkenyl, preferably containing from 2 to about 20 carbon atoms, more preferably from 2 to about 10 carbon atoms, further preferably from 2 to about 6 carbon atoms, further preferably from 2 and about 4 carbon atoms, for example ethenyl, propenyl, which may be linear or branched and may contain one or more heteroatoms, for example O, NH or S, (ii) an aldehyde, preferably containing from 1 to about 20 carbon atoms, more preferably from 1 to about 10 carbon atoms, further preferably from 1 to about 6 carbon atoms, further preferably from 1 to about 3 carbon atoms, for example —CHO or —R$^{17}$CHO, where $R^{17}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, (iii) hydrogen, and (iv) an ester, for example —C(O)OR$^{15}$ or —R$^{16}$C(O)OR$^{15}$, where $R^{15}$ is selected from (a) an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S, and (b) hydrogen, and where $R^{16}$ is an alkyl, preferably containing from 1 to about 20 carbon atoms, more preferably from 1 to about 10 carbon atoms, further preferably from 1 to about 6 carbon atoms, further preferably from 1 to about 3 carbon atoms, for example methyl, ethyl or propyl, which may be linear or branched and may contain one or more heteroatoms, for example O, NH or S.

In particularly preferred embodiments, the detectable marker comprises the structure shown in Formula IIA, and $R^1$ is absent or is selected from Mg$^{2+}$, Fe$^{2+}$, Zn$^{2+}$ or Cu$^{2+}$;
$R^2$ is CH$_3$ or CHO;
$R^3$ is CH$_2$CH$_3$ or CHCH$_2$;
$R^4$ is CH$_3$;
$R^5$ is H or C(O)OCH$_3$;
$R^6$ is CH$_2$CH$_2$COOH or CH$_2$CH$_2$C(O)OCH$_2$CH C(CH$_3$) CH$_2$CH$_2$CH$_2$CH(CH$_3$)CH$_2$CH$_2$CH$_2$CH(CH$_3$) CH$_2$CH$_2$CH$_2$CH(CH$_3$)CH$_3$;
$R^7$ is CH$_3$;
$R^8$ is CH$_3$;
$R^9$ is CHCH$_2$ or CHO;
$R^{12}$ is H;
$R^{13}$ is H; and
$R^{14}$ is H.

In other particularly preferred embodiments, the detectable marker comprises the structure shown in Formula IIB, and $R^1$ is absent or is selected from Mg$^{2+}$, Fe$^{2+}$, Zn$^{2+}$ or Cu$^{2+}$;
$R^2$ is CH$_3$ or CHO;
$R^3$ is CH$_2$CH$_3$ or CHCH$_2$;
$R^4$ is CH$_3$;
$R^6$ is CH$_2$CH$_2$COOH or CH$_2$CH$_2$C(O)OCH$_2$CH C(CH$_3$) CH$_2$CH$_2$CH$_2$CH(CH$_3$)CH$_2$CH$_2$CH$_2$CH(CH$_3$) CH$_2$CH$_2$CH$_2$CH(CH$_3$)CH$_3$;
$R^7$ is CH$_3$;
$R^8$ is CH$_3$;
$R^9$ is CHCH$_2$ or CHO;
$R^{10}$ is COOH;

$R^{11}$ is $CH_2COOH$;

$R^{12}$ is H;

$R^{13}$ is H; and $R^{14}$ is H.

In preferred embodiments, two of adjacent $R^2$ to $R^{14}$ are joined to form one or more 5 or 6-membered, optionally substituted, ring structures. For example, in relation to Formula IIA, $R^2$ and $R^3$, $R^3$ and $R^{12}$, $R^{12}$ and $R^4$, $R^5$ and $R^6$, $R^6$ and $R^7$, $R^7$ and $R^{13}$, $R^{13}$ and $R^8$, $R^8$ and $R^9$, $R^9$ and $R^{14}$, and/or $R^{14}$ and $R^2$ may be joined to form one or more 5 or 6-membered, optionally substituted, ring structures. For example, in relation to Formula IIB, $R^2$ and $R^3$, $R^3$ and $R^{12}$, $R^{12}$ and $R^4$, $R^4$ and $R^{10}$, $R^{10}$ and $R^{11}$, $R^{11}$ and $R^6$, $R^6$ and $R^7$, $R^7$ and $R^{13}$, $R^{13}$ and $R^8$, $R^8$ and $R^9$, $R^9$ and $R^{14}$, and/or $R^{14}$ and $R^2$ may be joined to form one or more 5 or 6-membered, optionally substituted, ring structures.

The nature of the ring structure will depend upon the nature of the groups forming the ring structure.

Preferably, the detectable marker comprises the structure shown in Formula IIB wherein $R^{10}$ and $R^{11}$ are joined to form a 5 or 6-membered, optionally substituted ring structure. The nature of the ring structure will depend upon the nature of $R^{10}$ and $R^{11}$. However, it will be appreciated that one such example of Formula IIB wherein $R^{10}$ and $R^{11}$ are joined to form a ring structure is the structure shown in Formula IIA.

Preferably, the detectable marker is selected from chlorophyll or a derivative, analogue or homologue thereof, or salt thereof. Preferably, the detectable marker is selected from chlorophyll a, b, c1, c2, or d or a derivative, analogue or homologue thereof, or salt thereof. In this respect, it is intended that the present invention encompasses phaeophytin, chlorophyllin, chlorophyllide, phaeophorbide and pyrophaeophorbide derivatives of chlorophyll a and b.

Preferably, the detectable marker is obtained from spirulina. For example, the detectable marker may be chlorophyll a obtained from Spirulina or a derivative, analogue or homologue thereof, or salt thereof.

Preferably, the detectable marker comprises concentrated chlorophyll extract from Lucerne or grass. Preferably, the detectable marker comprises phaeophorbide and phaeophytin.

Preferably, the detectable marker is selected from (i) a chlorophyllin, or a derivative, analogue or homologue thereof, or salt thereof, or (ii) a phaeophorbide or a derivative, analogue or homologue thereof, or salt thereof. Preferably, the detectable marker is selected from iron chlorophyllin, zinc chlorophyllin or magnesium chlorophyllin or a derivative, analogue or homologue thereof, or salt thereof.

In accordance with the above, the detectable marker may, for example, and without limitation, be selected from the structures shown below or derivatives, analogues or homologues thereof, or salts thereof. For the sake of conciseness, the structures shown below in relation to chlorophyllin, chlorophyllide, phaeophorbide, pyrophaeophorbide and phaophytin derivatives of chlorophyll are depicted as derivatives of chlorophyll a. However, it will be appreciated that the present invention also encompasses derivatives of chlorophyll b, c1, c2 and d.

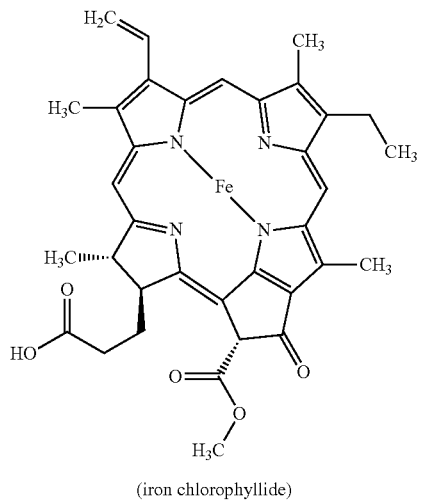

(iron chlorophyllide)

Formula III

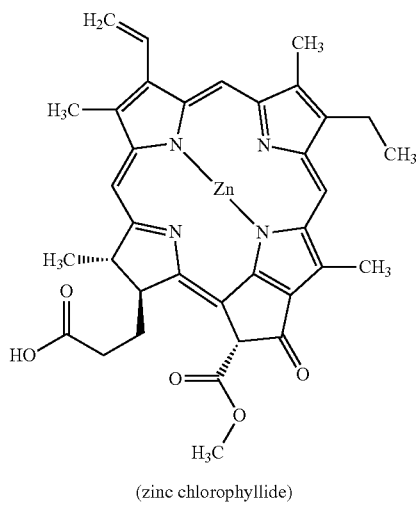

(zinc chlorophyllide)

Formula IV

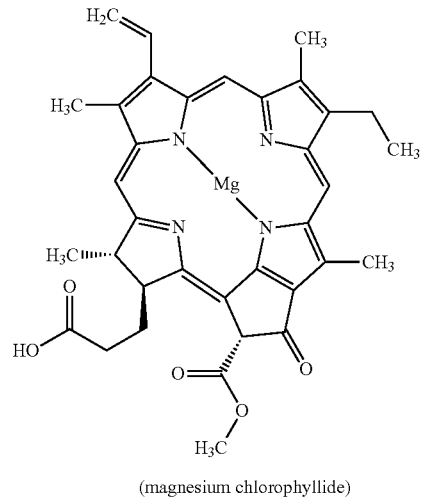

(magnesium chlorophyllide)

Formula V

Formula VI
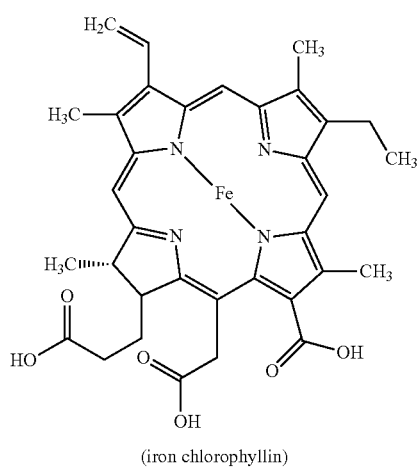
(iron chlorophyllin)
Formula VII
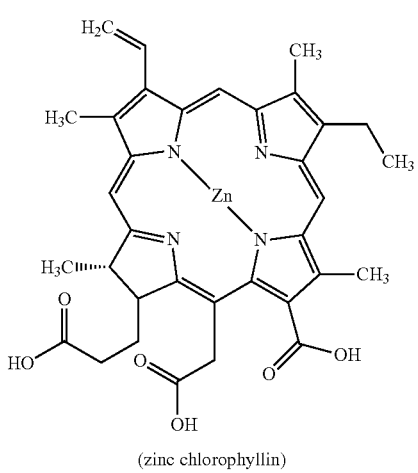
(zinc chlorophyllin)
Formula VIII
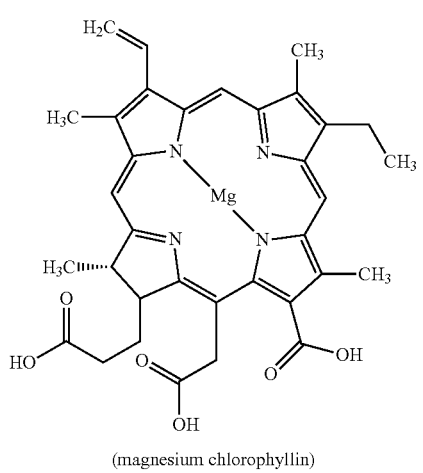
(magnesium chlorophyllin)
Formula IX
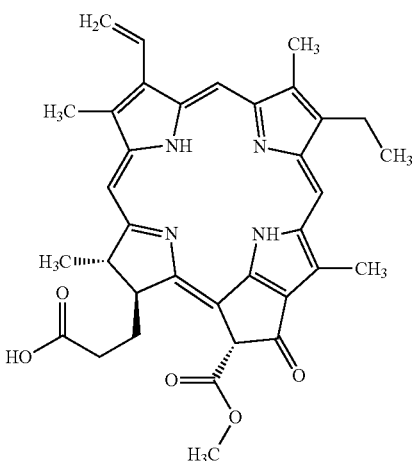
(phaeophorbide)
Formula X
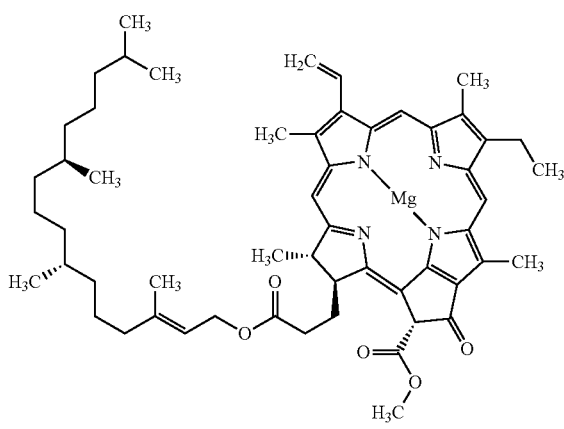
(chlorophyll a)
Formula XI
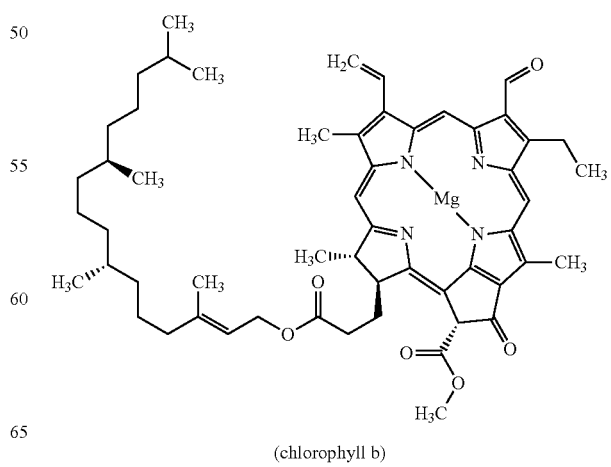
(chlorophyll b)

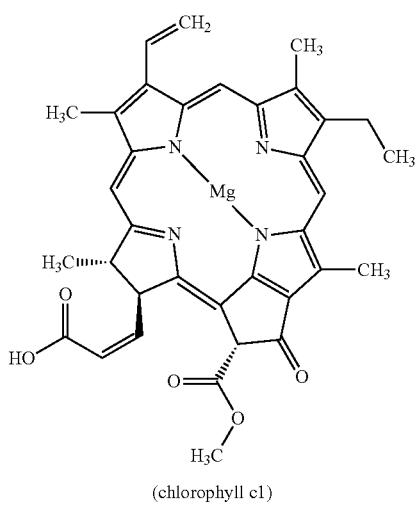

(chlorophyll c1) Formula XII

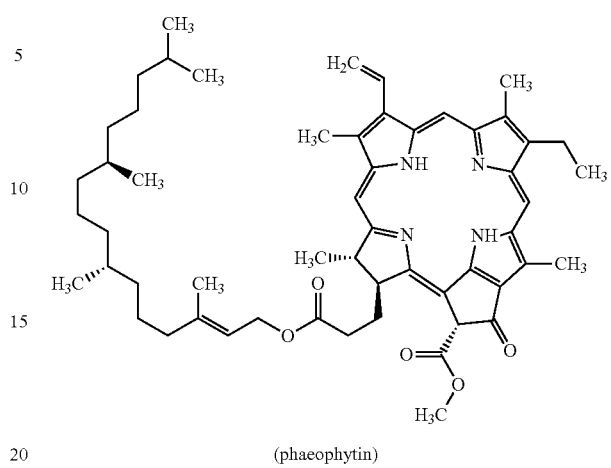

(phaeophytin) Formula XV

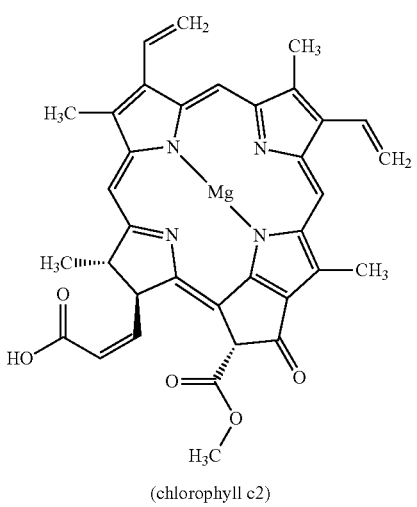

(chlorophyll c2) Formula XIII

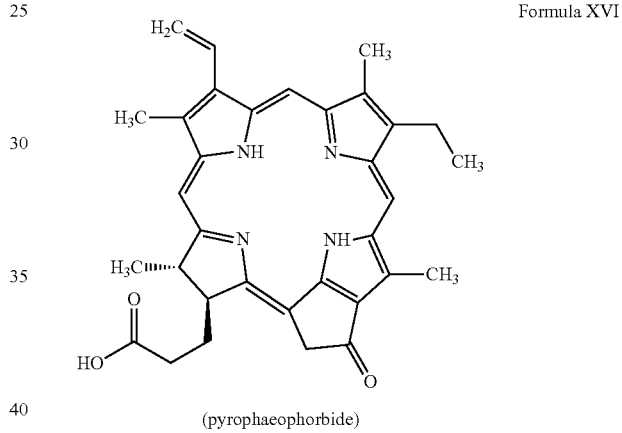

(pyrophaeophorbide) Formula XVI

As noted above, in preferred embodiments, the detectable marker comprises a salt of the aforementioned structures. Preferably the salt is a pharmaceutically acceptable salt. Non-limiting examples of wherein the detectable marker comprises a salt are as follows:

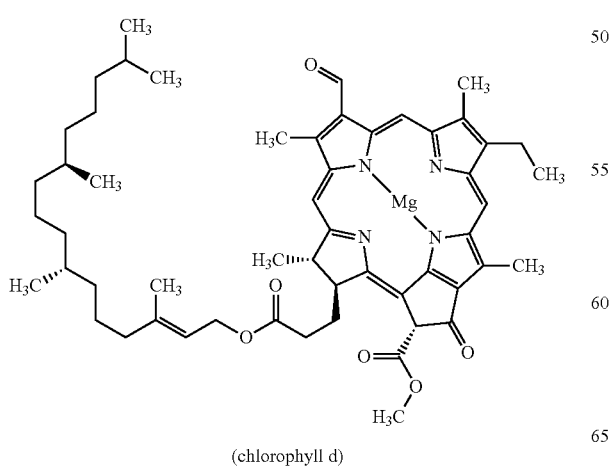

(chlorophyll d) Formula XIV

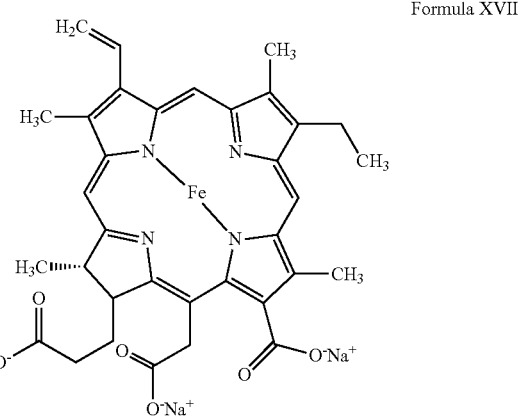

Formula XVII

-continued

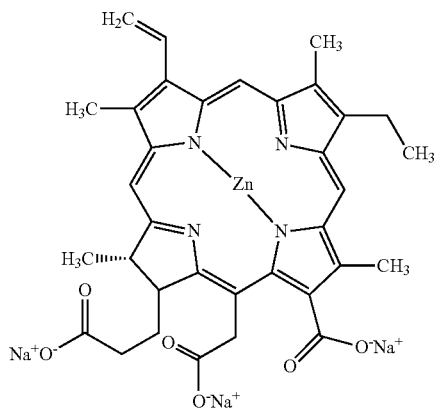

Formula XVIII

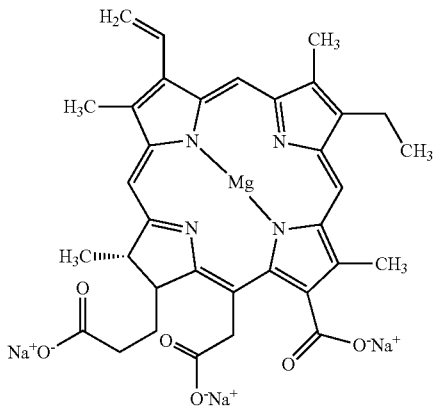

Formula XIX

Preferably, the animal carcass, meat obtained therefrom, or product is analysed at one or more stages of production. For example, analysis could be performed immediately after dissection and following each stage of processing thereafter. In addition, an analysis may be performed prior to packaging. Further analysis may be made before shipping the packaged produce.

Preferably, the animal is selected from bovine, poultry, porcine, ovine or caprine. However, it will be appreciated that the animal carcass, meat obtained therefrom, or product could be obtained from any animal in which faecal contamination during processing is a problem.

Preferably, the presence or absence of the detectable marker is determined via fluorescent spectroscopy.

Preferably, the detectable marker exhibits fluorescence at a wavelength of between about 660 nm and about 700 nm, preferably between about 670 nm and about 690 nm, preferably at about 685 nm.

Preferably, the detectable marker exhibits fluorescence at a wavelength of about 660 nm, for example 662 nm.

Preferably, the surface of the animal carcass, meat obtained therefrom, or product produced by or obtained from the animal is illuminated with UV or visible light having a wavelength effective to elicit fluorescence of the detectable marker. Preferably, the surface of the animal carcass, meat obtained therefrom, or product produced by or obtained from the animal is illuminated with light having a wavelength of between about 300 nm to about 600 nm, preferably between about 380 nm to about 440 nm or between about 510 nm to about 600 nm, preferably of about 400 nm.

For example, as described in the examples below, the animal carcass, meat obtained therefrom, or product produced by or obtained from the animal was illuminated at a wavelength of about 400 nm and the fluorescence detected at about 685 nm.

In some examples, the animal carcass, meat obtained therefrom, or product produced by or obtained from the animal is illuminated at a wavelength of about 380 nm or about 430 nm.

In some embodiments of the invention, detection of the detectable marker can be performed in accordance with the known methods described in International patent application number PCT/US99/03961, published under the number WO099/45138, the content of which is incorporated herein by reference in its entirety. As described therein, the ingesta and faeces of plant eating animals exhibit fluoresence at wavelengths between about 660 nm to about 680 nm when illuminated with appropriate UV or visible excitation light, such as light having wavelengths between about 300 nm to about 600 nm, particularly between about 400 nm to about 440 nm or 510 nm to 600 nm.

Preferably, the chlorophyll derivative, homologue or analogue thereof, or salt thereof is selected from a synthetic derivative, homologue or analogue thereof, or salt thereof or a naturally occurring derivative, homologue or analogue thereof, or salt thereof.

In preferred embodiments, the detectable marker is substantially stable during digestion in the animal gut. Put another way, it is preferred that the detectable marker is either not broken down during digestion, or is only broken down to a limited extent, such that the level of fluorescence in the faeces is substantially unaffected.

It will be appreciated that in the methods and compositions of the present invention, the detectable marker may comprise a combination of one or more detectable markers, for example a combination of one or more of the detectable markers described above. It will additionally be appreciated that a combination of chlorophyll and one or more of the derivatives, homologues or analogues, or salts thereof described above may be used in the methods and compositions of the present invention.

In preferred embodiments, the detectable marker is magnesium chlorophyllin.

As noted above, in some embodiments, the composition comprises a precursor for the detectable marker. For example, the composition may comprise a precursor for a chlorophyllin. In this respect, it is envisaged that once such a composition has been fed to an animal, the precursor will be modified in the gut of the animal, for example via digestive breakdown, such that the detectable marker will be detectable in the faeces of the animal.

Preferably, the composition has been fed to the animal for at least about 3 days before slaughter. Preferably, the composition has been fed to the animal for at least about 4 days, preferably at least about 5 days, preferably at least about one week prior to slaughter.

Preferably, prior to slaughter, the animal has been fed an effective amount of the detectable marker. For example, it is preferred that the animal has been fed a daily dose of at least about 1 g detectable marker per kg of dry matter intake, preferably at least about 2 g per kg of dry matter intake, preferably at least about 3 g per kg of dry matter intake, preferably at least about 4 g per kg of dry matter intake, preferably at least about 5 g per kg of dry matter intake, preferably at least about 10 g per kg of dry matter intake.

An "effective amount" refers to an amount of the detectable marker that is sufficient to enable the detectable marker to be reliably detected in the faeces of an animal.

Preferably, the composition is an animal feed or animal supplement. As such, there is provided an animal feed or animal supplement comprising a detectable marker or precursor thereof as described above for use in the methods of the present invention. In some embodiments, the animal feed or animal supplement is in the form of a liquid animal feed or animal supplement. In other embodiments, the animal feed or animal supplement is in the form of a dry animal feed or animal supplement, for example in the form of pellets.

Methods of production of animal feeds and animal supplements are known to a person skilled in the art. Accordingly, routine methods can be used to produce an animal feed or animal supplement of the present invention.

According to one aspect of the present invention, there is provided a method for analysing an animal carcass, meat obtained therefrom, or product produced by or obtained from the animal for the presence or absence of faecal matter, the method comprising:

analysing an animal carcass, meat obtained therefrom, or product produced by or obtained from the animal for the presence or absence of magnesium chlorophyllin, the presence of magnesium chlorophyllin being indicative of the presence of faecal matter and the absence of magnesium chlorophyllin being indicative of the absence of faecal matter;

wherein the animal carcass, meat obtained therefrom, or product produced by or obtained from the animal has been obtained from an animal fed a composition comprising a supplement of magnesium chlorophyllin or a precursor thereof.

Example embodiments of the present invention will now be described with reference to the accompanying figures.

Within this specification embodiments have been described in a way which enables a clear and concise specification to be written, but it is intended and will be appreciated that embodiments may be variously combined or separated without parting from the invention.

BRIEF DESCRIPTION OF THE DRAWINGS

FIG. 3 shows the positioning of faecal matter on a sample of meat as described further in Example 3;

FIGS. 4A and 4B show the results obtained from inspection of the meat sample in visible light (FIG. 4A) and using spectral imaging (FIG. 4B);

DETAILED DESCRIPTION OF THE INVENTION

Figure 1:
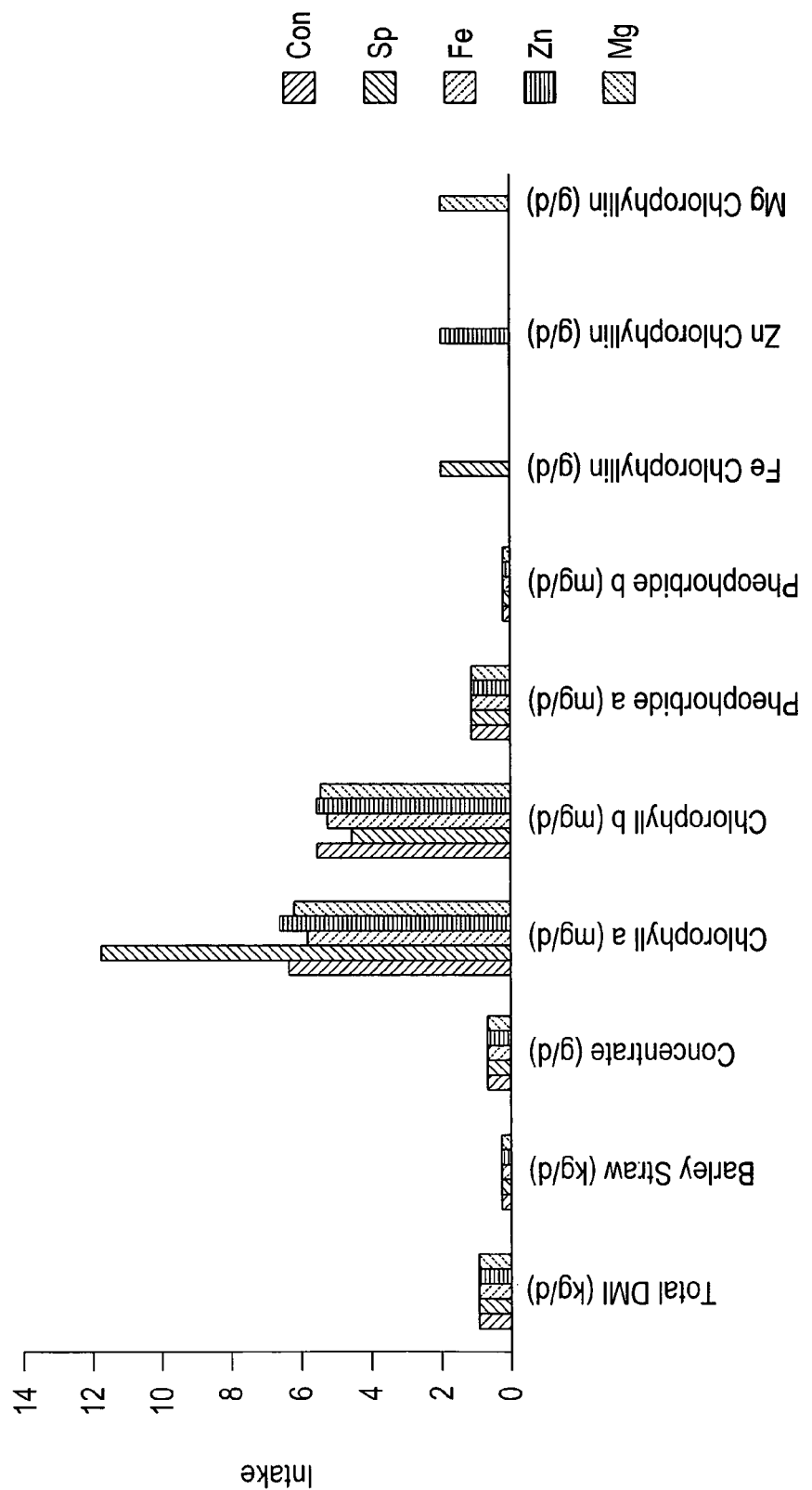
FIG. 1 shows the intakes of dry matter, chlorophyll, chlorophyll metabolites and the chlorophyllin markers on the five treatments described in Example 2.

The invention relates to methods for analysing an animal carcass, meat obtained therefrom, or product produced by or obtained from the animal for the presence or absence of faecal matter and compositions for use in such methods.

Examples of the invention are set out below.

Within this specification, the terms "comprises" and "comprising" are interpreted to mean "includes, among other things". These terms are not intended to be construed as "consists of only".

Within this specification, the term "about" means plus or minus 20%, more preferably plus or minus 10%, even more preferably plus or minus 5%, most preferably plus or minus 2%.

Within this specification, the term "animal" includes, for example, non-domestic livestock such as bovine, poultry, porcine, ovine or caprine. Specific examples include chickens, turkeys, cattle, pigs, sheep, and so on.

Within this specification, the term "derivatives" refers to molecules derived from the above-described compounds. Such derivatives may, for example, be digestion products of the above-described compounds or synthetically altered derivatives of the above described compounds. In this respect, it will be appreciated that if one of the above-described compounds is fed to an animal, then a derivative (e.g. a digestion product of the compound) may be detected in the methods described above. In this regard, it will be the derivative of the compound or the compound plus its derivative that will be comprised by the detectable marker. It will be appreciated that in some embodiments, the term "derivatives" encompasses metabolites of the above described compounds.

Within this specification, the term "homologues" refers to molecules having substantial structural similarities to the above-described compounds.

Within this specification, the term "analogues" refers to molecules having substantial biological similarities to the above-described compounds regardless of structural similarities.

Within this specification, the term "supplement" means an amount of detetectable marker or precursor thereof greater than that normally found in the basal diet of the animal to which the methods and compositions of the invention apply. For example, in the case of an animal fed a basal diet comprising grass then this basal diet will provide an intake of chlorophyll due to the chlorophyll content in the grass. In this case, a composition can be said to comprise a supplement of a detectable marker, e.g. chlorophyll, if the level of detectable marker in the composition is higher than that normally found in the basal grass diet of the animal. It will be appreciated that a naturally occurring supplement of a detectable marker may fall under the meaning of the term "supplement" as long as it provides a higher (or "supplemented") level of detectable marker when compared to the basal diet of the animal.

Within this specification, the term "alkenyl" means an organic radical formed from an unsaturated aliphatic hydrocarbon. The alkenyl may have one, two or three double bonds, preferably one double bond in a straight or branched chain. Examples of alkenyl groups are ethenyl, 1-propenyl, 2-propenyl, 2-butenyl, 2-methyl-1-propenyl, or 3-methyl-2-butenyl.

Within this specification, the term "alkyl" means an organic radical formed from a saturated aliphatic hydrocarbon. Examples of alkyl groups are methyl, ethyl, propyl, isopropyl, butyl, isobutyl, sec-butyl, pentyl or hexyl.

Within this specification, the term "pharmaceutically acceptable salt" means a salt that retains the desired activity of the parent compound and does not impart undesired toxicological effects. Examples of pharmaceutically acceptable salts are discussed in Berge et al., 1977, "Pharmaceutically Acceptable Salts," J. Pharm. ScL, Vol. 66, pp. 1-19.

EXAMPLES

In vivo whole tract digestion studies were used to identify the best chlorophyll breakdown products for use as markers of faecal contamination on a range of diets altering in their chlorophyll concentration and chlorophyll breakdown products as a consequence of conservation differences (e.g. hay versus silage). The breakdown of chlorophyllin compounds on these diets was also assessed. Chlorophyllin is a semi-synthetic derivative of chlorophyll. It is used in the feed industry as a food colourant, to reduce odour from a colostomy or ileostomy and also as an aid to reduce faecal odour due to incontinence. It is envisaged that chlorophyllin or natural chlorophyll markers could be used as a feed additive prior to slaughter and in diets of animals fed predominantly grain based diets for easy assessment of faecal contamination of the carcass. Once candidate marker compounds were identified their efficacy was assessed using spectroscopic imaging and multi-spectral imaging of contaminated meat.

Example 1

A number of chlorophyll breakdown products was tested for use as markers of faecal contamination on a range of diets. Eight Cheviot sheep were fed either: i) fresh grass and clover, ii) grass silage, iii) hay or iv) concentrate and barley straw. Each diet was offered to two sheep for a period of two weeks before diet change over in a duplicate 4×4 Latin Square design. Samples of feed were collected during the whole feeding period and bulked whilst samples of faeces were taken at the end of the period. Samples were measured for chlorophyll and its derivatives using HPLC. Fluorescence emission spectra were measured directly on the faeces. The samples were placed into sample cuvettes, which exposed a flat circular surface with a diameter of 5 cm for the measurements. The fluorescence emission spectra were measured with excitation at 382 nm and 430 nm, using an optical bench system, suitable for solutions and solid samples. The excitation light was generated by a 300 W Xenon light source (Oriel 6258, Oriel Corporation, Stratford, Conn.) and passed through a 10 nm bandwidth interference filter (Oriel 59920) and (Oriel 59295). The light was directed onto the samples at an angle of about 45°. The spectra were collected by an imaging spectrograph (Acton SP-150, Acton Research Corporation, Acton, Mass.) connected to a sensitive charge coupled device (CCD-camera) (Roper Scientific NTE/CCD-1340/400-EMB, Roper Scientific, Trenton, N.J.). Cut-off filters at 400 nm (for the 382 nm excitation) (Melles Griot 03FCG049) and 475 nm (for the 430 nm excitation) (Melles Griot 03FCG068) were positioned in front of the spectrograph slit to suppress excitation light reflected from the samples. Exposure time was 10 seconds and 5 seconds for excitation at 382 nm and 430 nm, respectively. The temperature of the samples was 4° C. All the samples were measured twice and an average was used in the analysis. The field of illumination was not perfectly homogenous, so the samples were rotated 90° between each measurement to even out sample heterogeneity. To ensure stable illumination, the emission intensity at 440 nm at excitation 382 nm was measured from a stable fluorescence standard of washable plastic (Ciba, Basel, Switzerland) before and after the measurements. Fluorescence images were collected with the same system, slightly modified. A Nikon 102 mm photographic lens was mounted on the imaging spectrograph, the spectrograph slit was removed and the grating was exchanged with a mirror. Spectral images were created by placing a 40 nm bandwidth interference filter in front of the lens. Samples were illuminated by 400 nm (10 nm bandwidth filter, Melles Griot 03FIV026) light and images were captured at 685 nm (10 nm bandwidth). Exposure time for each image was 60 seconds.

Animals offered the fresh grass and clover diets had a greater concentration of fluorescent compounds in their faeces and subsequent fluorescence than animals on conserved forages and on concentrate based diets. Consequently the accuracy of the spectral imaging detection of faecal contamination depended on the diet of the animal. This is why previous techniques such as 'Verifeye®' have not been universally accepted.

Example 2

Ten male sheep (Cheviots) were allocated at random to one of five treatments: Control (C, no marker); zinc chlorophyllin (Zn, 2 g/d); iron chlorophyllin (Fe, 2 g/d); magnesium chlorophyllin (Mg, 2 g/d) or chlorophyll a from spirulina (Sp, 2 g/d). The experiment consisted of two 5×5 Latin Squares. Each period consisted of two weeks. The first week had no supplementation of marker and acted as the adaptation and wash-out period with all animals receiving ad libitum concentrate (Wynnstay, Lamb master) and barley straw. The second week animals received 2 g/d of marker mixed with a handful of damp concentrate given to the animals before feeding to ensure that the marker was consumed. Marker supplementation was based on the intake of chlorophyll per day from silage diets (Lee et al. J Anim Sci, 84: 3061-3070; 2006), the content of which is incorporated herein by reference in its entirety. During the dosing week animals were fed ad libitum barley straw and concentrate at 30% above maintenance (MJ/d=1.15$\{0.25*(W/1.08)0.75\}$ where W is liveweight in kg). Faecal collection occurred for 1 day after each 2 week period. Animals were removed from stalls to a clean concrete floored collection area and left for 2 hours, after which time clean faeces (no food or bedding contamination) was collected. Animals were weighed at the start and end of each experimental period, with daily intakes monitored during the feeding of the marker. The faecal samples (circa 100 g) for each animal were split in two and frozen at −80° C. Half were prepared for spectral imaging and the other half for chlorophyll metabolite analysis.

Figure 2:
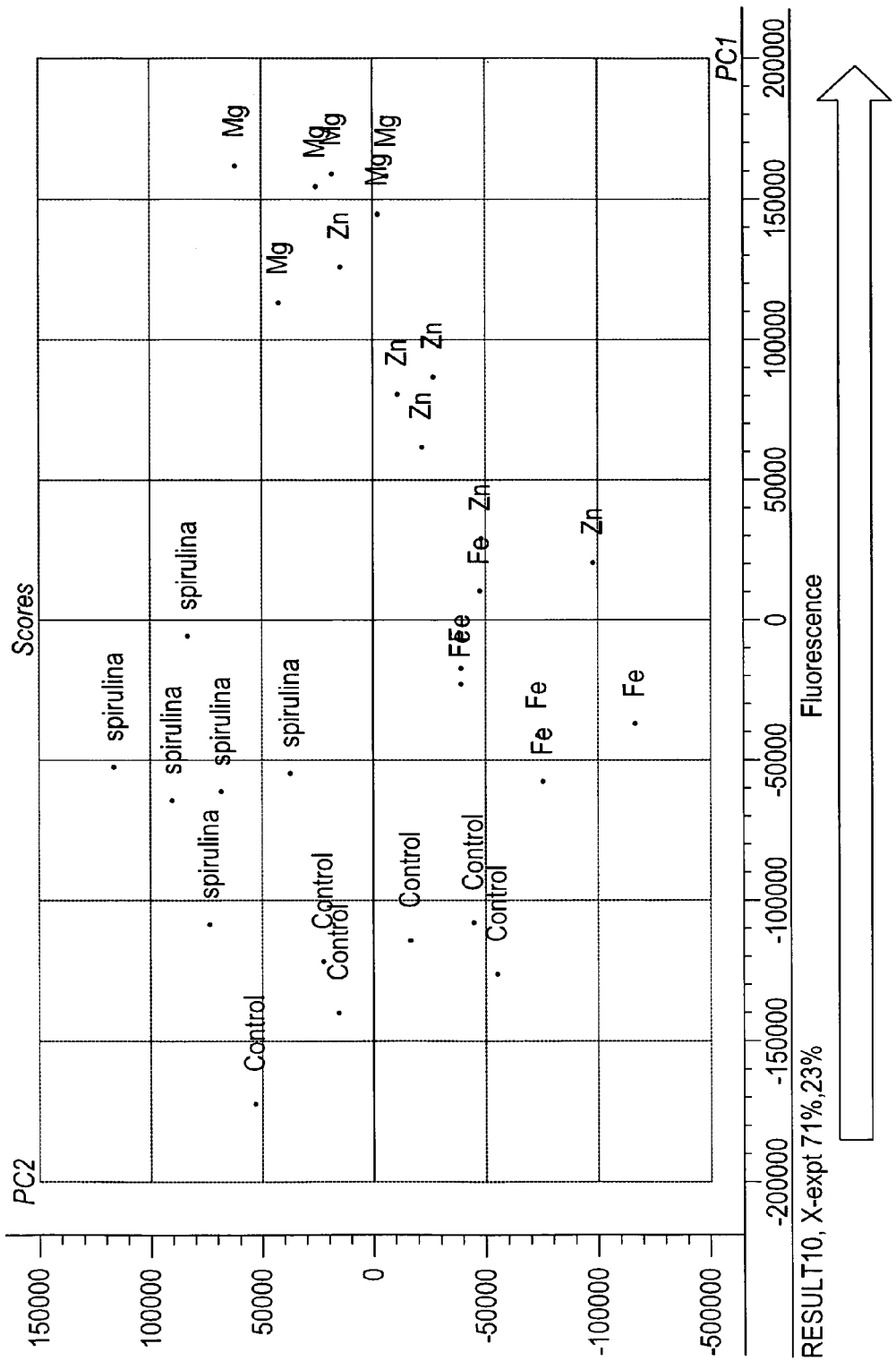
FIG. 2 shows PCA (Principal Component Analysis) of the fluorescence of faeces from sheep given four different markers.

Intakes of dry matter, chlorophyll, chlorophyll metabolites and the chlorophyllin markers on the five treatments are shown in FIG. 1. The addition of the markers did not affect dry matter intake. Intake of chlorophyll a was significantly ($P<0.001$) higher on the Sp (chlorophyll a from spirulina) treatment but was similar on all other treatments along with the metabolite pheophorbide. FIG. 2 clearly shows that the spectral pattern of the faeces is different across the markers and shows the potential of each marker to specifically fluorescently mark faeces.

Example 3

A meat sample was taken and contaminated at separate locations on the meat with faeces taken from each of the five treatments performed in Example 2 (as shown in FIG. 3).

As shown in FIG. 4A, all five faecal samples were detectable on the meat in visible light. In addition, when viewed using spectral imaging, all five faecal samples were detectable (excitiation at 400 nm, captured at 685±5 nm) (FIG. 4B).

Figure 5A:
FIGS. 5A and 5B show the results obtained from inspection of the meat sample in visible light (FIG. 5A) and using spectral imaging (FIG. 5B) once the faecal matter had been brushed off the meat sample.
Figure 5B:

However, when the faeces were removed from the meat sample (but not rinsed off), the faecal samples were barely detectable on the meat in visible light (FIG. 5A) and whilst faeces taken from animals fed the chlorophyllin supplemented treatment were detectable using spectral imaging (excitiation at 400 nm, captured at 685±5 nm) (FIG. 5B), the faeces taken from an animal fed the control diet was barely detectable.

Figure 6A:
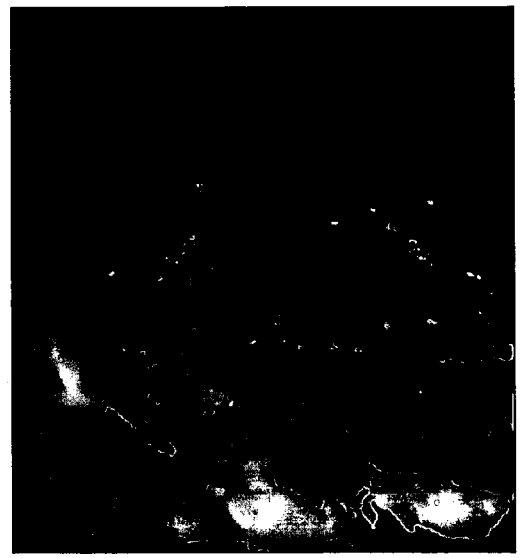
FIGS. 6A and 6B show the results obtained from inspection of the meat sample in visible light (FIG. 6A) and using spectral imaging (FIG. 6B) once the meat sample had been rinsed with water.
Figure 6B:
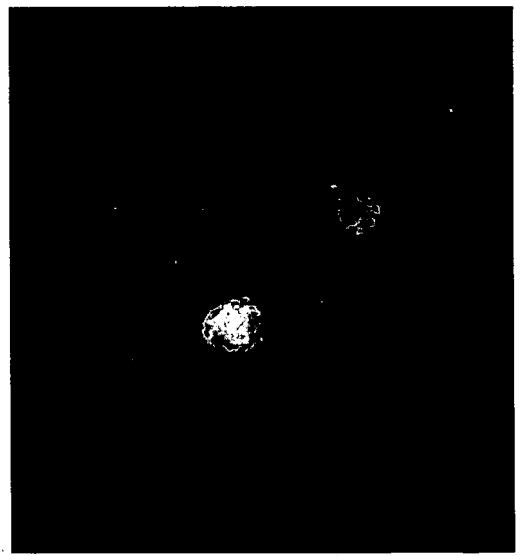
Figure 7:
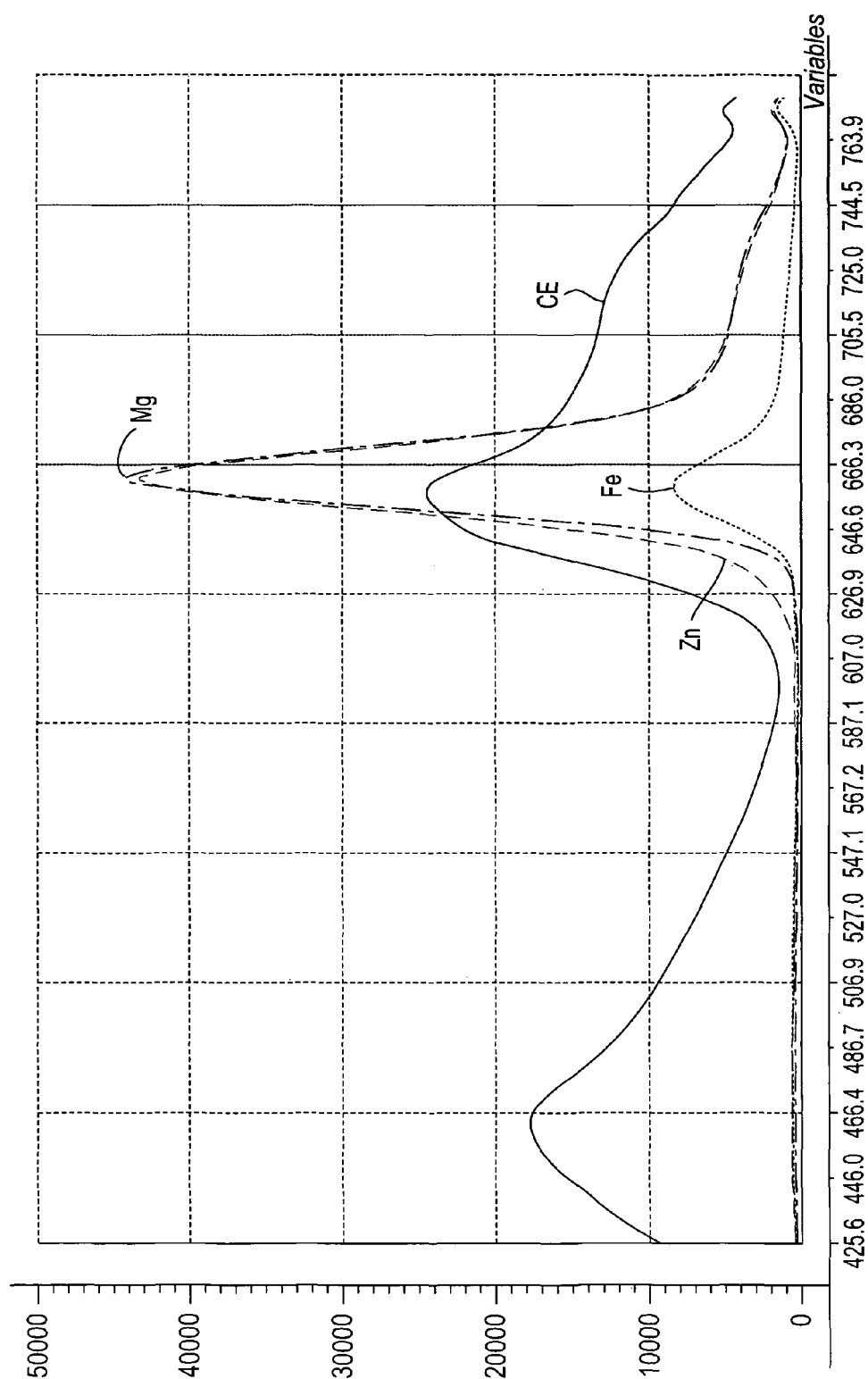
FIG. 7 shows emission spectra of four markers (Mg chlorophyllin, Fe chlorophyllin, Zn chlorophyllin and chlorophyll extract) using an excitation $\lambda=380$ nm.
Figure 8:
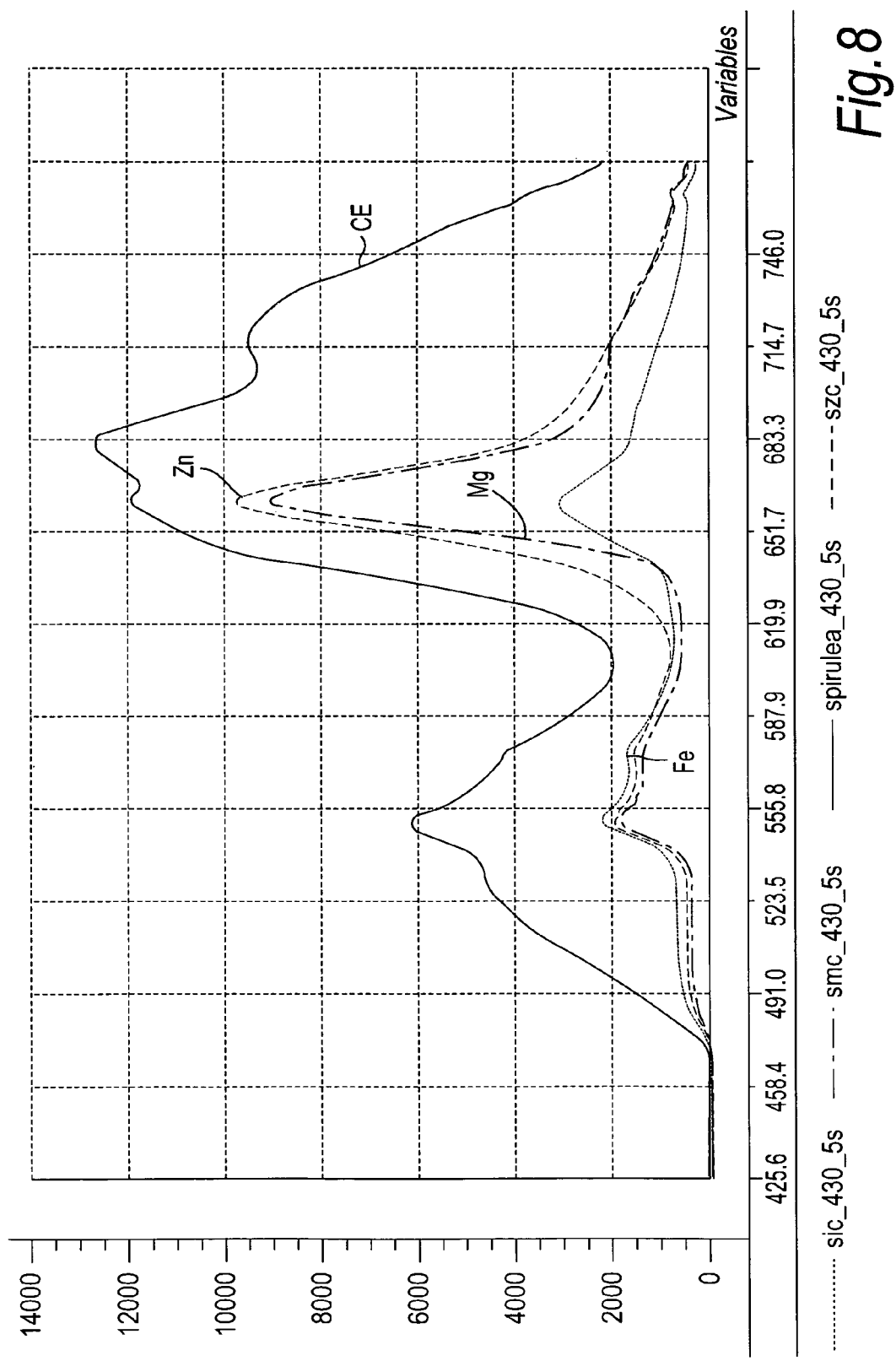
FIG. 8 shows emission spectra of four markers (Mg chlorophyllin, Fe chlorophyllin, Zn chlorophyllin and chlorophyll extract) using an excitation $\lambda=430$ nm.

When the meat sample was rinsed with water, none of the faecal samples was detectable on the meat in visible light (FIG. 6A) nor were the faeces taken from an animal fed the control diet detectable using spectral imaging (excitiation at 400 nm, captured at 685±5 nm). However, as shown in FIG. 6B, faeces taken from animals fed the chlorophyllin supplemented treatment were detectable using spectral imaging.

As evidenced above, when using a supplement of chlorophyllin markers, the markers can be found in the faeces of sheep. The chlorophyllin markers Fe, Zn and Mg produced fluorescence in faeces and would be suitable as markers. Spirulina through its chlorophyll a content also produced fluorescence in faeces. This suggests that a pure form of chlorophyll a could also be used as a marker in diets fed to animals before slaughter. The highest level of fluorescence was seen in the Mg Chlorophyllin.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

The invention claimed is:

1. A method for analysing an animal carcass, meat obtained therefrom, or product produced by or obtained from an animal for the presence or absence of faecal matter, the method comprising:
    analysing the animal carcass, meat obtained therefrom, or product produced by or obtained from the animal for the presence or absence of a detectable marker, the presence of the detectable marker being indicative of the presence of faecal matter and the absence of the detectable marker being indicative of the absence of faecal matter;
    wherein the animal carcass, meat obtained therefrom, or product produced by or obtained from the animal has been obtained from an animal fed a composition comprising a supplement of the detectable marker and/or a precursor thereof;
    wherein the detectable marker is zinc chlorophyllin, iron chlorophyllin, magnesium chlorophyllin or copper chlorophyllin, or a derivative, analogue or homologue thereof, or salt thereof.

2. A method according to 1, wherein the animal carcass, meat obtained therefrom, or product produced by or obtained from the animal is analysed at one or more stages of production.

3. A method according to claim 1, wherein the animal is selected from bovine, poultry, porcine, ovine or caprine.

4. A method according to claim 1, wherein the presence or absence of the detectable marker is determined via fluorescent spectroscopy.

5. A method according to claim 1, wherein the detectable marker exhibits fluorescence at a wavelength of between about 660 nm and about 700 nm.

6. A method according to claim 4, wherein the surface of the animal carcass, meat obtained therefrom, or product produced by or obtained from the animal is illuminated with UV or visible light having a wavelength effective to elicit fluorescence of the detectable marker.

7. A method according to claim 6, wherein the surface of the animal carcass, meat obtained therefrom, or product produced by or obtained from the animal is illuminated with light having a wavelength of between about 300 nm to about 600 nm.

8. A method according to any of claim 4, wherein the animal carcass, meat obtained therefrom, or product produced by or obtained from the animal is illuminated at a wavelength of about 400 nm and the fluorescence is detected at about 685 nm.

9. A method according to claim 1, wherein the composition has been fed to the animal for at least about 3 days before slaughter.

10. A method according to claim 1, wherein, prior to slaughter, the animal has been fed an effective amount of the detectable marker.

11. A method according to claim 10, wherein the animal has been fed a daily dose of at least about 2 g detectable marker per kg of dry matter intake.

12. A method according preceding claim 1, wherein the detectable marker is substantially stable during digestion in the animal gut.

13. A method according to claim 1, wherein the product produced by or obtained from the animal is selected from eggs and milk.

* * * * *